US012612350B2

(12) United States Patent
Zhou et al.

(10) Patent No.: US 12,612,350 B2
(45) Date of Patent: Apr. 28, 2026

(54) OZONOLYSIS OF POLYCYCLIC AROMATIC HYDROCARBONS IN LIQUID CO₂

(71) Applicant: University of Kansas, Lawrence, KS (US)

(72) Inventors: Huaxing Zhou, Warwick, PA (US); Abhimanyu O. Patil, Westfield, NJ (US); Bala Subramaniam, Lawrence, KS (US); Timothy A. Jackson, Lawrence, KS (US); Andrew M. Danby, Bishop Wilton (GB); Honghong Shi, Lawrence, KS (US); Michael D. Lundin, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 467 days.

(21) Appl. No.: 18/271,735

(22) PCT Filed: Jan. 13, 2021

(86) PCT No.: PCT/US2021/013169
§ 371 (c)(1),
(2) Date: Jul. 11, 2023

(87) PCT Pub. No.: WO2022/154782
PCT Pub. Date: Jul. 21, 2022

(65) Prior Publication Data
US 2024/0076259 A1     Mar. 7, 2024

(51) Int. Cl.
*C07C 45/40*     (2006.01)
*C07C 29/48*     (2006.01)

(52) U.S. Cl.
CPC .............. *C07C 45/40* (2013.01); *C07C 29/48* (2013.01); *C07C 2602/10* (2017.05)

(58) Field of Classification Search
CPC ...... C07C 45/40; C07C 29/48; C07C 2602/10
See application file for complete search history.

(56) References Cited

U.S. PATENT DOCUMENTS

| | | |
|---|---|---|
| 10,730,814 B2 | 8/2020 | Subramaniam et al. |
| 2019/0177254 A1 | 6/2019 | Subramaniam et al. |
| 2019/0248723 A1 | 8/2019 | Subramaniam et al. |
| 2022/0112339 A1 | 4/2022 | Subramaniam et al. |

FOREIGN PATENT DOCUMENTS

| | | |
|---|---|---|
| EP | 2 399 897 A1 | 12/2011 |
| WO | WO 2008/077769 A1 | 7/2008 |
| WO | WO 2022/192866 | 9/2022 |

OTHER PUBLICATIONS

The International Search Report and Written Opinion issued on Aug. 10, 2021 for PCT/US2021/013169; pp. 1-8.

*Primary Examiner* — Sikarl A Witherspoon
(74) *Attorney, Agent, or Firm* — Bell & Manning, LLC

(57) ABSTRACT

Systems and methods are provided for ozonolysis of polycyclic aromatic hydrocarbons (PAHs) in a liquid CO₂ reaction environment. It has been unexpectedly discovered that oxygen-containing functional groups can be added to PAH substrates while substantially avoiding combustion reactions and while reducing or minimizing formation of energetic intermediates. Because the formation of energetic intermediates is minimal, the ozonolysis can be performed at temperatures near ambient (e.g., between −10° C. and 50° C.) while still achieving a satisfactory safety profile. In various aspects, ozonolysis can occur while forming a reduced or minimized amount of water, such as forming substantially no water in the reaction environment.

20 Claims, 4 Drawing Sheets

OZONOLYSIS OF POLYCYCLIC AROMATIC HYDROCARBONS IN LIQUID CO$_2$

This application is a National Stage of International Application No. PCT/US2021/013169, filed Jan. 13, 2021, the entire contents of which are herein incorporated by reference.

FIELD OF THE INVENTION

This invention relates to systems and methods for ozonolysis of polycyclic aromatic hydrocarbons in a liquid CO$_2$ reaction environment.

BACKGROUND OF THE INVENTION

Polycyclic aromatic hydrocarbons (PAHs) are a class of chemicals that occur naturally in coal and crude oil. During crude oil processing, PAHs tend to concentrate in less volatile fractions such as vacuum resids. They are also formed as a burning byproduct of fossil fuels, wood, garbage and tobacco. Due to the highly aromatic nature of PAHs, even if hydrogenation is performed on the PAHs, the value of the hydrocarbons remains relatively low. When combined with the high hydrogen requirements for hydrogenation of PAHs, the value of the products from hydrogenation of PAHs is typically not sufficient to justify the cost of performing hydrogenation.

As an alternative to hydrogenation, PAHs such as tetralin, phenanthrene, biphenyl, fluorene and pyrene have the potential to be transformed to aromatic variants possessing new functional groups such as aldehyde and/or carboxylic acid with minimal loss of carbon. Such compounds can be valuable precursors for making a host of new materials with tunable properties for specific applications including easily recyclable polymers and fibers.

Unfortunately, efficiently creating such functional groups in PAHs using conventional oxidation techniques employing oxidants such as dioxygen remains a challenge. Conventional methods for oxidizing PAHs using O$_2$ as the oxidant typically require high temperatures. However, this results in a significant fraction of the substrate (i.e., PAHs) being lost to combustion.

To overcome the difficulties with using O$_2$ as an oxidant, some efforts have focused on oxidation of PAHs using ozone in an organic solvent environment. Oxidation of PAHs using ozone has been reported to yield oxygenated products such as dialdehydes and carboxylic acids with high selectivity and yields. However, such reported ozonolysis of PAHs is usually performed at low temperatures (e.g. −78° C. in a dry ice-methanol bath). The low temperatures are used in part to slow down the formation and potential decomposition of energetic intermediates. Such intermediates can be unstable even at ambient temperatures. Without careful control, the decomposition of such energetic intermediates can result in reaction runaway conditions and accidents. Thus, the reaction environment is typically maintaining at temperatures well below −50° C. in order to reduce or minimize the potential risks associated with conventional ozonolysis.

Another challenge with reported ozonolysis studies is the stability of conventional organic solvents to ozone attack and the formation of flammable vapors. Due in part to limited solubility of PAHs in various organic solvents, the organic solvent used to provide the ozonolysis reaction environment is typically present in a large excess relative to the amount of PAHs. Any reactions of ozone with the organic solvent can reduce the amount of O$_3$ available for the substrate. In order to reduce or minimize loss of O$_3$ due to reaction with the organic solvent, halogenated solvents such as chloroform have been used as reaction media. Although halogenated solvents are relatively inert to O$_3$ and are typically non-flammable, halogenated solvents are also known to be toxic and damaging to the environment. This makes halogenated solvents an undesirable option in a commercial production setting.

It would be desirable to have improved methods for adding oxygen-containing functional groups to PAHs that is suitable for use in commercial settings. Preferably, the methods would allow for addition of oxygen-containing functional groups while reducing or minimizing side reaction that result in formation of CO$_2$. Additionally, the methods would allow for addition of oxygen-containing functional groups while reducing or minimizing the potential for hazardous conditions related to the reaction environment.

U.S. Pat. No. 10,730,814 describes methods for selective oxidation of alkanes by ozonolysis in a liquid CO$_2$ reaction environment.

SUMMARY OF THE INVENTION

In an aspect, a method for conversion of polycyclic aromatic hydrocarbons is provided. The method includes exposing a feedstock comprising one or more polycyclic aromatic hydrocarbons to ozonolysis conditions in a reactor volume containing liquid CO$_2$ to convert at least a portion of the one or more polycyclic aromatic hydrocarbons into oxygenated conversion products. The ozonolysis conditions can include a temperature of −25° C. to 50° C. and a pressure of 1.0 MPa-a to 15 MPa-a. The ozonolysis conditions can further include a molar ratio of O$_3$ to the one or more polycyclic aromatic hydrocarbons in the reaction medium of 0.1 or more.

DETAILED DESCRIPTION OF THE EMBODIMENTS

Figure 1:
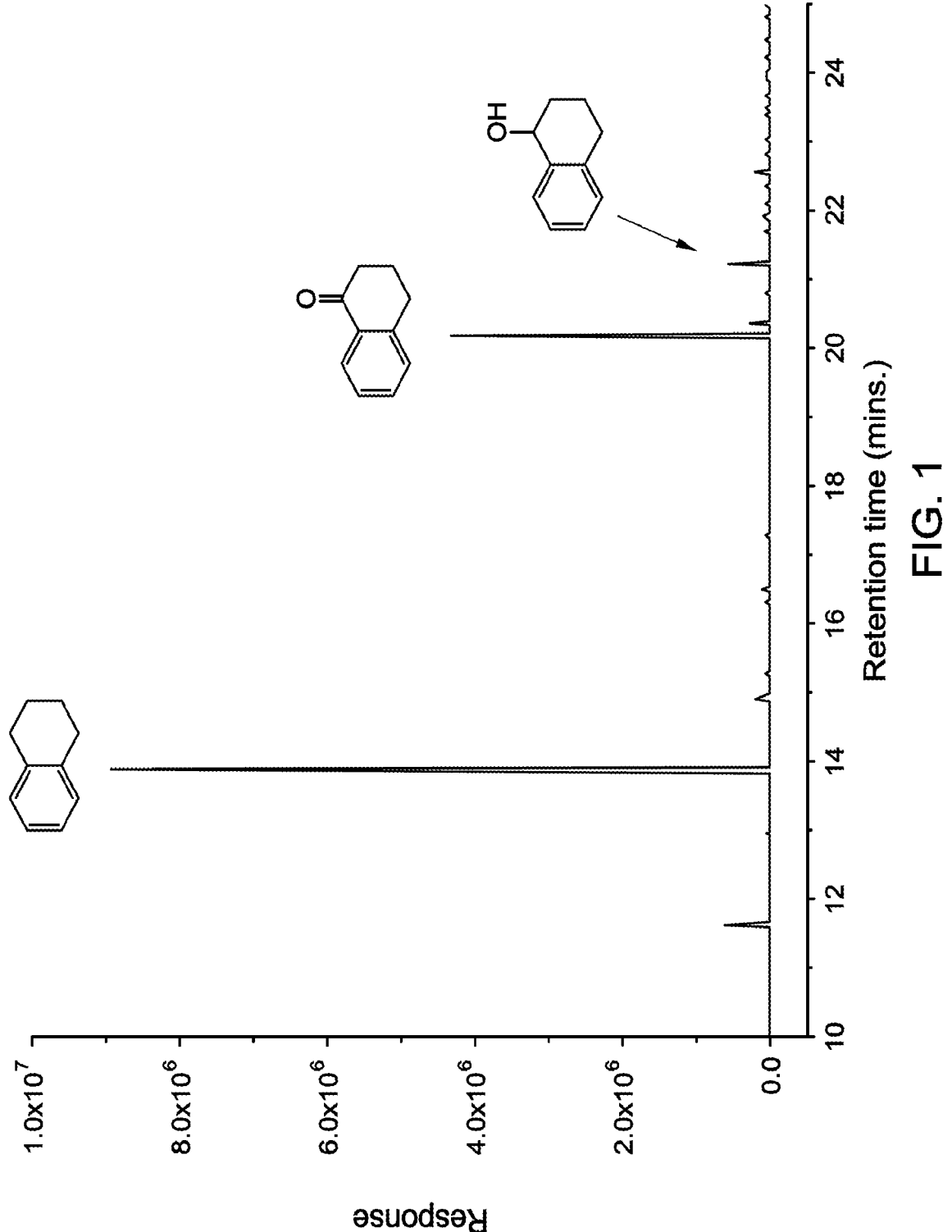
FIG. 1 shows a GC-MS spectrum of products from ozonolysis of tetralin.

All numerical values within the detailed description and the claims herein are modified by "about" or "approximately" the indicated value, and take into account experimental error and variations that would be expected by a person having ordinary skill in the art.

Overview

In various aspects, systems and methods are provided for ozonolysis of polycyclic aromatic hydrocarbons (PAHs) in a liquid CO$_2$ reaction environment. It has been unexpectedly discovered that oxygen-containing functional groups can be added to PAH substrates while substantially avoiding combustion reactions and while reducing or minimizing formation of energetic intermediates. In particular, it has been discovered that ozonolysis of PAHs in liquid CO$_2$ yields oxygenated products such as dialdehydes, acids and oligomers thereof without evidence of detectable undesirable ozonides and peroxides (energetic species) as intermediate species. Because the formation of energetic intermediates is minimal, the ozonolysis can be performed at temperatures near ambient (e.g., between −10° C. and 50° C.) while still achieving a satisfactory safety profile. With regard to combustion, because the reaction environment is liquid $CO_2$, it would be difficult to detect the presence of carbon oxides formed by combustion. However, the reaction environment can initially be substantially free of water and so the presence or absence of substantial combustion can be detected based on monitoring the formation of water in the reaction environment. In various aspects, ozonolysis can occur while forming a reduced or minimized amount of water, such as forming substantially no water in the reaction environment. Forming substantially no water is defined as water corresponding to less than 1.0 wt % of the reaction products, relative to the weight of PAHs that are converted under the ozonolysis conditions.

Part of the unexpected nature of the ozonolysis results for PAHs in a liquid $CO_2$ reaction environment was due to the uncertainty of how a $CO_2$ solvent might interact with the ozonolysis reaction pathway(s). For conventional ozonolysis of PAHs in organic solvents, one of the difficulties is that the potential for formation of energetic reaction intermediates requires the use of temperatures below −50° C. in order to maintain a desirable level of control over reaction conditions. Similar concerns with formation of energetic reaction intermediates are also present for ozonolysis of alkenes. For example, when alkenes are exposed to ozonolysis conditions in a liquid $CO_2$ reaction environment, such energetic intermediates are formed. Thus, based on how ozonolysis proceeds for alkenes in liquid $CO_2$, it could be expected that ozonolysis of PAHs in a liquid $CO_2$ reaction environment would also result in formation of energetic intermediates. For ozonolysis of polyaromatic hydrocarbons, some potential reaction products of ozonolysis correspond to stable intermediates and/or products, while others (such as gem diperoxides and/or certain types of secondary ozonides) are undesirable energetic intermediates. It was unknown how the liquid $CO_2$ reaction environment would interact with the ozonolysis reaction intermediates, and whether such interactions would facilitate and/or suppress the formation of the undesirable energetic intermediates. It has been discovered that ozonolysis of PAHs can be performed in a liquid $CO_2$ reaction environment without formation of the undesirable energetic intermediates. In particular, based on $^{13}$C-NMR analysis of reaction products, the undesirable gem-diperoxides and energetic secondary intermediates are not formed (and/or are formed in a reduced or minimized amount) during ozonolysis of PAHs in liquid $CO_2$.

In addition to reducing or minimizing the formation of energetic intermediates, performing ozonolysis of PAHs in a liquid $CO_2$ reaction environment also provides a more desirable reaction environment for scaling of the ozonolysis process to commercial scale operation. First, liquid $CO_2$ can provide sufficient solubility to dissolve PAHs and perform ozonolysis at a commercial scale. Additionally, the presence of dense $CO_2$ (a flame retardant) in the vapor phase reduces, minimizes, or eliminates flammability concerns.

In some aspects, the liquid $CO_2$ reaction environment can be supplemented with a co-solvent that is relatively inert with respect to reactions with $O_3$. Acetic acid is an example of a co-solvent that has low reactivity with $O_3$, but that can assist with solubilizing PAHs in the reaction environment.

Polycyclic Aromatic Hydrocarbons (PAHs)

Polycyclic aromatic hydrocarbons refer to hydrocarbons that include a) a plurality of ring structures and b) at least one aromatic ring structure. Naphthalene and tetralin are examples of PAHs. Naphthalene is a structure that includes a total of two aromatic rings. Partial hydrogenation of naphthalene to saturate one of the rings can result in formation of tetralin. Tetralin includes a plurality of ring structures in the form of one aromatic ring and one non-aromatic ring. Although tetralin includes a fully saturated ring, it is noted that a "non-aromatic" ring can include one or more degrees of unsaturation, so long as the ring is not aromatic. Further hydrogenation of the tetralin would hydrogenate the remaining aromatic ring, and therefore would result in a compound that is not a polycyclic aromatic hydrocarbon In some aspects, a polycyclic aromatic hydrocarbon can include two or more aromatic rings, or three or more aromatic rings, or four or more aromatic rings, such as up to seven aromatic rings or possibly still higher. Additionally or alternately, in some aspects a polycyclic aromatic hydrocarbon can include one or more non-aromatic rings, or two or more non-aromatic rings, or three or more, such as up to five non-aromatic rings or possibly still higher. Further additionally or alternately, in some aspects ozonolysis can be performed on polycyclic aromatic hydrocarbons including three or more total rings, or four or more total rings, or five or more total rings, such as up to seven total rings or possibly still higher.

A feedstock including PAHs can correspond to a feed that contains one or more other types of hydrocarbons and/or one or more other types of feed components. For example, in some aspects a feedstock including PAHs can correspond to a portion of an atmospheric reside fraction, a vacuum reside fraction, an unconverted bottoms fraction (from a refinery process such as coking, hydroprocessing, or slurry hydroprocessing), or another convenient fraction that includes PAHs. In other aspects, the feedstock including PAHs can correspond to at least a portion of a deasphalter rock fraction from a solvent deasphalting process or an aromatic extract fraction from a solvent extraction process that uses an aromatic solvent. The amount of PAHs in a feedstock can correspond to 5.0 wt % or more of the feedstock to the ozonolysis process, or 10 wt % or more, or 20 wt % or more, or 40 wt % or more, or 60 wt % or more, or 80 wt % or more, such as up to having substantially all of the feedstock correspond to PAHs. For example, the amount of PAHs in the feedstock can correspond to 5.0 wt % to 25 wt % of the feedstock, or 5.0 wt % to 50 wt %, or 10 wt % to 25 wt %, or 10 wt % to 50 wt %.

Conditions for Ozonolysis of PAHs

In various aspects, ozonolysis of a feedstock containing PAHs can be performed in a liquid $CO_2$ reaction environment. Because the reaction environment corresponds to a liquid $CO_2$ reaction environment, some of the reaction conditions are selected based in part on the need to maintain a substantially liquid $CO_2$ environment within the reactor vessel containing the reaction environment. In various aspects, 80 wt % or more of the compounds in the reaction environment (and/or the reactor vessel containing the reaction environment) can be $CO_2$, or 90 wt % or more, or 95 wt % or more, such as up to 99.5 wt % or possibly still higher.

Generally, liquid $CO_2$ can be formed at temperatures of roughly −56° C. or greater. However, in various aspects it can be desirable to have a reaction temperature that is closer to ambient temperatures. In such aspects, the temperature of the liquid phase medium (i.e., the $CO_2$ and any reactants within the liquid phase $CO_2$) can be −25'C to 75° C., or −25°

C. to 50° C., or −25° C. to 25° C., or −10° C. to 75° C., or −10° C. to 50° C., or −10° C. to 25° C. It is noted that a temperature of 30° C. or less is below 31.1° C., which is the critical temperature for substantially pure $CO_2$. Thus, in some aspects the temperature of the liquid phase medium can be selected to be below the critical temperature for $CO_2$.

The pressure of the reaction environment is defined herein as the total pressure of the vapor phase/dense phase present over the liquid phase medium. Generally, liquid $CO_2$ can be formed at pressures of roughly 510 kPa-a or greater. In various aspects, the pressure can be 1.0 MPa-a or more, or 2.0 MPa-a or more, or 3.0 MPa-ii or more, or 4.0 MPa-a or more, such as up to 1.5 MPa-a or possibly still higher. It is noted that the critical pressure of substantially pure $CO_2$ is roughly 7.4 MPa-a. In some aspects, the pressure of the reaction environment can be selected to be below the critical pressure for $CO_2$. Alternatively, if the reaction environment is completely filled with the liquid phase, then the pressure of the reaction environment is defined as the pressure of the liquid phase.

In this discussion, a $CO_2$ phase used as a reaction environment is defined as a liquid phase reaction environment when the temperature and pressure of the reaction environment result in a condensed fluid phase of $CO_2$ being present. This corresponds to a) conditions where substantially pure $CO_2$ is a liquid at equilibrium or b) conditions where the pressure is greater than the critical pressure for substantially pure $CO_2$ (roughly 7.4 MPa-a) and the temperature is between the triple point temperature (roughly −56° C.) and the critical temperature (roughly 31° C.). Thus, a liquid phase medium for the reaction environment does not include conditions where substantially pure $CO_2$ corresponds to a supercritical fluid (i.e., temperature greater than 31° C. and pressure greater than 7.4 MPa-a).

In addition to the $CO_2$ that is used as the liquid phase medium, the reaction environment can also include an oxidant and a feedstock that contains PAHs. In various aspects, the oxidant can correspond to $O_3$. For practical reasons when using $O_3$ as an oxidant, other compounds may be introduced along with the oxidant and/or as part of an oxidant stream. For example, $O_3$ can be made from $O_2$ using commercially available ozone generation methods. This results in a gas stream that includes both $O_3$ and $O_2$. For example, commercial grade ozone generators can convert a substantially pure stream of $O_2$ into a gas flow including 14 vol %-20 vol % $O_3$ in $O_2$. Optionally, after forming a stream containing both $O_3$ and $O_2$, additional $O_2$ can be blended into the stream to achieve a lower concentration of $O_3$ if desired. Additionally, if the $O_2$ stream used to generate ozone includes $N_2$, the $N_2$ can also be passed into the resulting ozone-containing stream.

In various aspects, an ozone-containing stream for use as an oxidant, can include 1.0 vol % to 20 vol % $O_3$ relative to the total volume of the ozone-containing stream, or 1.0 vol % to 15 vol %, or 5.0 vol % to 20 vol %, or 5.0 vol % to 15 vol %, 1.0 vol % to 10 vol %, or 5.0 vol % to 10 vol %. Optionally, the ozone-containing stream can include 0.1 vol % to 20 vol % $N_2$, or 0.1 vol % to 10 vol. % $N_2$, or 0.1 vol % to 5 vol % $N_2$. In other aspects, the ozone-containing stream can include substantially no $N_2$ (less than 0.1 vol %). The balance of the ozone-containing stream can preferably correspond to $O_2$. Optionally, the ozone-containing stream can include 5.0 vol % or less of compounds other than $O_3$, $O_2$, and $N_2$, or 1.0 vol % or less, or 0.1 vol % or less. Examples of other compounds that can be present in an ozone-containing stream include $CO_2$ and $H_2O$.

The relative amounts of hydrocarbons and oxidant present in the liquid phase medium can be selected so that an excess of $O_3$ is present relative to the amount of $O_3$ required for stoichiometric reaction with the hydrocarbons. In various aspects, the molar ratio of $O_3$ to total hydrocarbons in the liquid phase medium can be between 0.1 and 50 (i.e., between 0.1 moles $O_3$ per mole hydrocarbon to 50 moles $O_3$ per mole hydrocarbon), or between 1.0 and 50. Additionally or alternately, the molar ratio of $O_3$ to total PAHs in the liquid phase medium can be between 0.1 and 50, or 1.0 and 50.

In some aspects, the hydrocarbon and oxidant content in the reaction environment can be managed based on introduction of fresh feeds of hydrocarbons and oxidants into the reaction environment. In other aspects, recycle can be used to allow for further reaction of hydrocarbons that do not react during a single pass through the reaction system. In such aspects, the molar ratio of recycled PAHs to PAHs in fresh feed can be between 0.1 to 10, or 0.1 to 5.0, or 0.5 to 10, or 0.5 to 5.0, or 1.0 to 10, or 1.0 to 5.0. In various aspects, the molar ratio of $O_3$ to hydrocarbons in fresh feed can be between 1.0 to 250, Or 1.0 to 50, or 5.0 to 250, or 5.0 to 50. A portion of the oxidant can also be recycled, if desired.

It is noted that both $O_3$ and some PAHs can potentially have limited solubility within liquid $CO_2$ as a liquid phase medium, so that the molar ratio of $O_3$ to PAHs in the liquid phase medium may not necessarily reflect the molar ratio of $O_3$ to PAH introduced into the reaction environment. In some aspects, the concentration of PAHs in the liquid phase medium can be 1.0 moles of PAH or less per liter of liquid $CO_2$, or 0.3 moles of PAH or less per liter of liquid $CO_2$, or 0.1 moles of PAH or less per liter of liquid $CO_2$, or 0.01 moles of PAH or less per liter of liquid $CO_2$, such as down to $1.0 \times 10^{-4}$ moles of PAH per liter of liquid $CO_2$ or possibly still lower.

Optionally, the liquid phase medium can further include a co-solvent such as acetic acid. In aspects where a co-solvent is used in addition to $CO_2$ such as a co-solvent to facilitate dissolution of PAHs in the liquid phase medium), the molar ratio of the co-solvent to in the reaction environment can be 0.01 to 0.15 (i.e., 0.01 moles to 0.15 moles of co-solvent per mole of $CO_2$ in the reaction environment).

The PAHs can be maintained in the liquid phase medium for a sufficient time to achieve a desired level of ozonolysis. In some aspects, the residence time for the PAHs in the liquid phase medium in the presence of $O_3$ can be 60 minutes or less, or 30 minutes or less, or 20 minutes or less, such as down to 0.1 minutes or possibly still less. In a continuous flow reactor, the residence time can correspond to an average residence time based on flow rate(s) into and/or out of the reactor. In a batch flow reactor, the residence time can correspond to reaction time, such as the amount of time the reaction environment within the reactor is maintained at the desired reaction conditions.

In various aspects, the ozonolysis conditions can allow for single-pass conversion of 10 wt % or more of the PAHs in a feedstock into oxygenated products, or 25 wt % or more, or 50 wt % or more, such as up to converting substantially all of the PAHs in a feedstock. In aspects where recycle is used, the ozonolysis conditions can allow for net conversion of 10 wt % or more of the PAHs in a feedstock into oxygenated conversion products, or 25 wt % or more, or 50 wt % or more, such as up to converting substantially all of the PAHs in a feedstock. Conversion of PAHs results in formation of oxygenated conversion products. Oxygenated conversion products are defined as products formed during ozonolysis that include at least one oxygen atom from ozone and at least one additional atom from a PAH. Thus, water or carbon oxides formed as a combustion product is included within the definition of an oxygenated conversion product.

Optionally but preferably, the conversion can be performed while reducing or minimizing formation of combustion products, so that 3.0 wt % or less of the oxygenated products correspond to water and/or $CO_2$, or 1.0 wt % or less, or 0.1 wt % or less, such as down to forming substantially no combustion products.

Example—Solubility of PAHs in $CO_2$

Solubility of various PAHs was determined (qualitatively) in liquid $CO_2$ and supercritical $CO_2$. The PAH substrates tested included cyclohexane, benzene, 1,2,3,4-tetrahydronaphthalene (tetralin), naphthalene, biphenyl, fluorine, and phenanthrene. The PAH substrates were obtained commercially (high purity grades) and used as received. In a typical dissolution experiment, 0.5 g of a solid substrate or 1.0 mL of a liquid substrate was added to a 20 ml high pressure reactor vessel. The reactor was then sealed and pressurized with liquid $CO_2$ (604 psi, 6° C.) or supercritical $CO_2$ (1250 psi, 34° C.). Ultrasonic mixing was utilized to aid the dissolution. The qualitative results are as shown in the Table 1. For comparison, the solubility of cyclohexane and benzene was also tested.

TABLE 1

| | Solubility in $CO_2$ | |
| --- | --- | --- |
| PAH Substrate | Solubility in Liquid $CO_2$ | Solubility in Supercritical $CO_2$ |
| Cyclohexane | Yes | Yes |
| Benzene | Yes | Yes |
| Tetralin | Yes | Yes |
| Naphthalene | Partial | Partial |
| Biphenyl | Partial | Partial |
| Fluorene | Partial | Mostly |
| Phenanthrene | Slight | |

In Table 1, 'Yes' means that the compounds were completely soluble in $CO_2$ at all attempted concentrations. 'Slight' means that a discoloration of the $CO_2$ was observed indicating something had entered solution, but the original material remained largely unaffected. 'Partial' and 'Mostly' represent solubility levels where at least a portion of the compounds clearly were dissolved in solution, but at least some solid material remained undissolved.

As shown in Table 1, a variety of polyaromatic hydrocarbons have more than sufficient solubility in liquid $CO_2$ to allow for ozonolysis in a liquid $CO_2$ medium. In addition to the above substrates, it is noted that the solubility of methyl-substituted phenanthrene is similar to the solubility for phenanthrene. It is believed that alkyl substitution of PAHs will similarly have a small impact on solubility in liquid $CO_2$.

Example—Ozonolysis of Tetralin

Ozonolysis of tetralin was performed in a laboratory scale apparatus. The apparatus included a 20 ml high-pressure cell vessel equipped with an ultrasonic horn, a pressure transducer, a thermocouple, and sampling and pressure relieve valves. Real-time temperature and pressure values were recorded. Temperature control was achieved with an insulated cooling jacket surrounding the reactor vessel through which a heat-transfer liquid was circulated.

In a typical experiment, 0.4 ml of tetralin (0.0029 mol) was placed in a 20 ml reactor cell. Reactor is sealed and pressurized with $CO_2$ to 4.4 MPa-a at 8° C. The tetralin/$CO_2$ solution is observed to be clear without color at this moment.

The lower flammability limit (LEL) for tetralin in air is 0.8% and the upper flammability limit (UFL) in air is 5.0%. The low vapor pressure of tetralin at the operating conditions ensures that the vapor phase is below the LFL. The quantity of substrate is such that the adiabatic temperature rise at total combustion will not lead to runaway conditions.

An ISCO pump is used to compress a mixture of ozone in oxygen (roughly 10 wt % ozone) into the reactor cell to a total cell pressure of 96.5 bar. The clear solution turns brown initially then black within a few seconds upon addition of ozone which is recognized as the start of reaction. As the reaction proceeds, the color of solution gradually fades and eventually disappears within 30 minutes as the ozone is consumed. Precipitate is formed on the reactor inner wall as observed on the sapphire windows. Following $O_3$ consumption (i.e., disappearance of the coloration of the reactor contents), the reactor was depressurized for 60 minutes. Either hexane or acetone was used to wash the cell for product collection upon sonication (one minute).

Gas chromatography—mass spectrometry (GC-MS) analysis was used to identify the products. FIG. 1 shows the resulting GC-MS spectrum. As shown in FIG. 1, in addition to the tetralin peak, two significant product peaks (α-tetralone and α-tetralol) were observed. The product distribution indicates that the $C_1$ aliphatic carbon is preferentially attacked by the $O_3$ during the ozonation rather than the $C_5$-$C_{10}$ aromatic carbons.

Example—Ozonolysis of Phenanthrene

In a typical ozonolysis experiment, 0.55 mmol (0.1 g of phenanthrene) or 1.1 mmol of substrate (0.2 g of phenanthrene) was placed in a 20 ml reactor cell and cooled to approximately 8° C. The cell was filled with liquid $CO_2$ with a dip tube until approximately 10 mL of liquid $CO_2$ was present. The saturation vapor pressure for liquid $CO_2$ at this temperature is approximately 621 psi (~4.2 MPa). Ozone introduction into the reactor cell was achieved with an ISCO pump, whose cylinder was initially filled with an $O_3$ in $O_2$ stream from an ozone generator at ambient pressure and room temperature. Following complete dissolution of substrate under sonication in liquid $CO_2$, the $O_3$/$O_2$ mixture in the ISCO pump was compressed (by reducing the cylinder volume at 200 mL/min) to approximately 700 psi (~4.8 MPa), which is slightly greater than the saturation pressure of liquid $CO_2$ in the view cell maintained at 8° C. The inlet valve to the reactor cell was then opened to gradually pump $O_3$/$O_2$ mixture into the cell at 25 mL/min (corresponding to the reduction in ISCO pump cylinder volume). The pumping rate was regulated to minimize temperature rise caused by gas compression in the fixed-volume view cell upon addition of the $O_3$/$O_2$ mixture. Sufficient $O_3$/$O_2$ was added to increase the pressure to a level that resulted in a target molar ratio of $O_3$ to phenanthrene of either roughly 16 (for 0.1 g phenanthrene) or roughly 8.0 (for 0.2 g phenanthrene). The start of this pressurization step (after the inlet valve is opened) takes approximately 1.5 minutes and signals the start of the ozonation reaction. The reaction was allowed to proceed for 30 min.

In a first run, 0.1 a cell including 0.1 g (0.55 mmol) of phenanthrene was exposed to a roughly 16:1 molar ratio of $O_3$ to phenanthrene. When the $O_3$/$O_2$ gas was introduced into the reactor, a view window for the cell turned opaque. As the reaction proceeded, the cell became translucent again and some solids (suspected to be ozonides) precipitated on the sapphire window. At around 120 minutes, the blue/purple color of ozone almost completely faded away, and the $CO_2$ was slowly released from the reactor cell over 30 minutes. 2 mL of deuterated acetone (acetone-d6) solvent was injected into the reactor to recover the products for $^{13}C$ NMR and $^1H$ NMR analysis. Afterwards, 20 mL of non-deuterated acetone solvent was added to the reactor cell for a complete wash, and the cell wash solution was analyzed using GC-MS analysis. It was observed that some solids remained insoluble in acetone and are not soluble in either methanol or toluene. Based on the high solubility of phenanthrene in acetone (estimated at roughly 34.33 g in 100 g acetone at 8° C.), it is believed that the insoluble solid is not unreacted phenanthrene.

Figure 2:
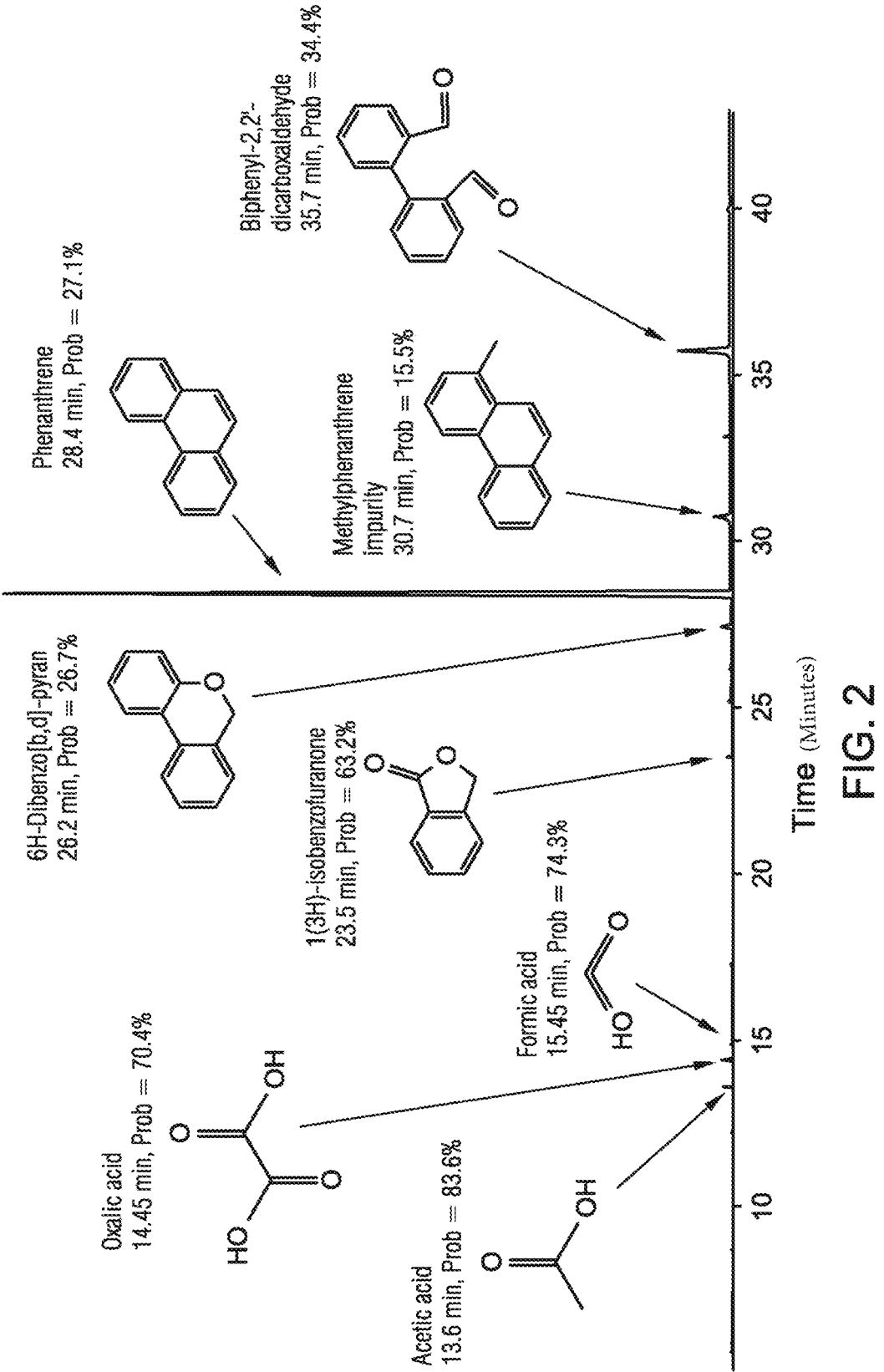
FIG. 2 shows a GC-MS spectrum of products from ozonolysis of phenanthrene.

FIG. 2 shows the results from the GC-MS analysis of the acetone-soluble solid product. In FIG. 2, lines with arrow heads connect the chemical structures with the corresponding peak in the spectrum. Lines without arrowheads connect the names to the chemical structures. As shown in FIG. 2, analysis of the acetone-soluble solid product by GC-MS reveals diphenylaldehyde as the likely product (shown as the peak at 35.7 min in FIG. 2), although the probability assigned by the mass spectrometer was somewhat low (roughly 34%). In addition, some single benzene-ring aromatic compounds and some $C_1$-$C_2$ carboxylic acids were detected by the GC-MS suggesting decomposition of an ozonide intermediate or the phenanthrene. A significant amount of phenanthrene was detected in the acetone solution suggesting that the phenanthrene conversion is low.

Figure 3:
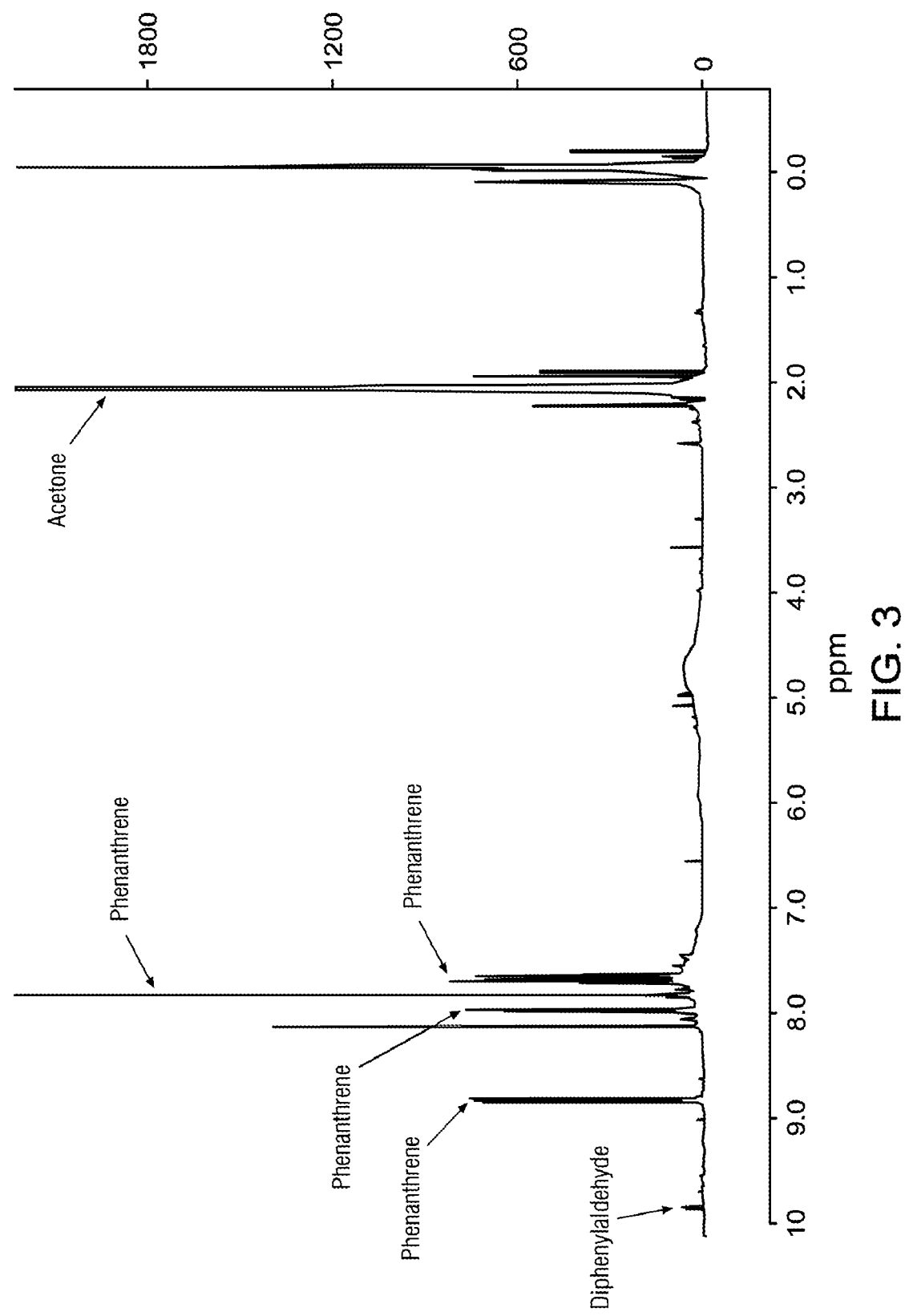
FIG. 3 shows a $^1$H NMR spectra of products from ozonolysis of phenanthrene.

FIG. 3 shows the $^1H$ NMR spectra of the products recovered in the deuterated acetone wash. As shown in FIG. 3, the products recovered in the deuterated acetone wash showed a significant aldehyde group peak at 9.7 ppm, which suggests the formation of diphenylaldehyde as found in the GC-MS results.

Figure 4:
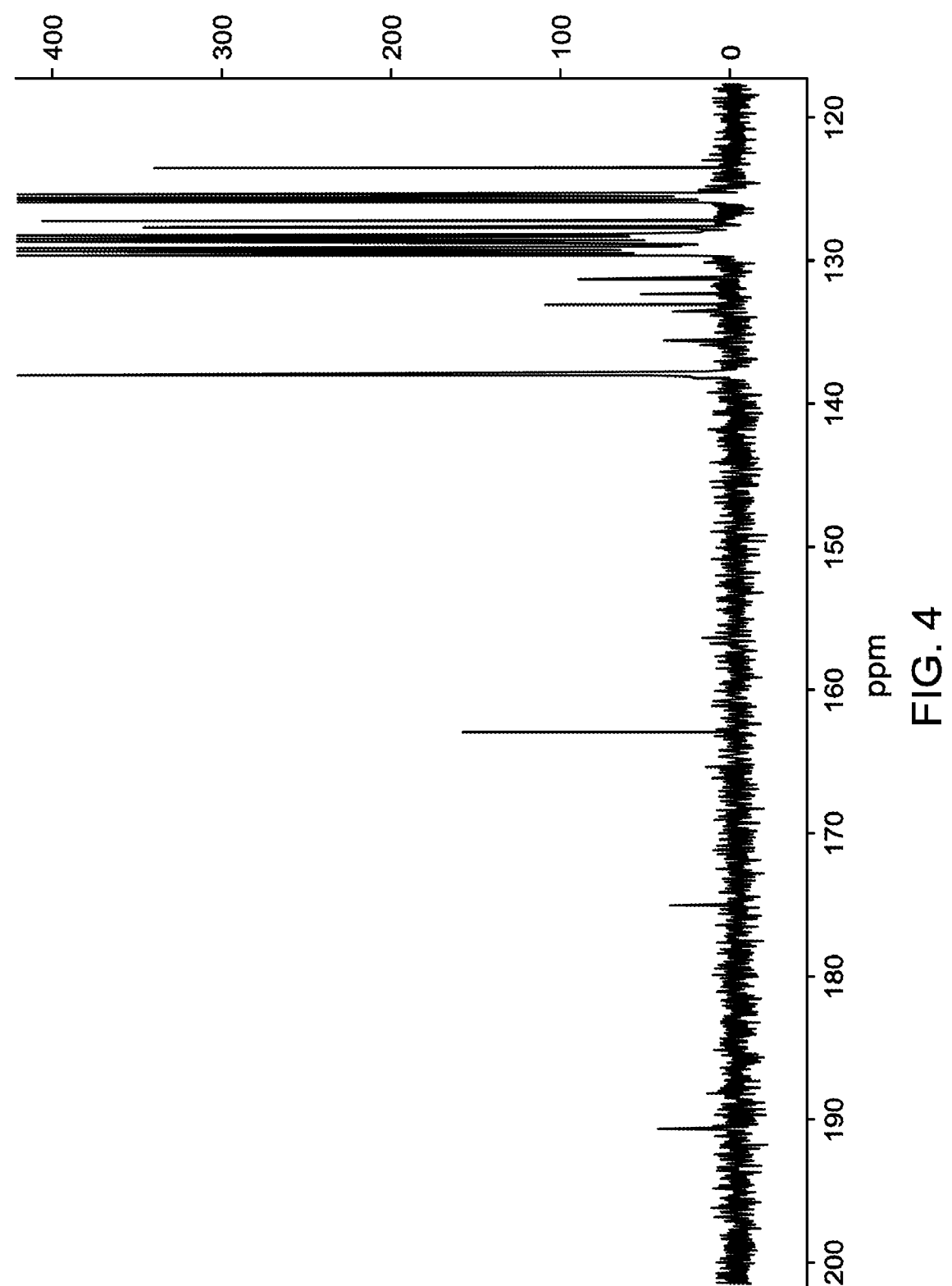
FIG. 4 shows a $^{13}$C NMR spectra of products from ozonolysis of phenanthrene.

Additional runs were performed where 0.2 g (1.1 mmol) of phenanthrene were loaded into the reactor cell. In one run, ozonolysis was started immediately after performing 4 hours of sonication to dissolve the phenanthrene in the liquid $CO_2$. In another run, after sonication to dissolve the phenanthrene, the solution was allowed to rest overnight under pressure at 8° C. prior to starting ozonolysis. For the run where ozonolysis was performed after resting overnight, products were once again formed that were insoluble in acetone, methanol, or ethanol. However, for the run where ozonolysis was performed immediately after sonication, all products were soluble in at least one of acetone, methanol, or ethanol. This indicates a possible change in reaction pathway. For the run where ozonolysis was performed immediately after sonication, $^{13}C$ NMR analysis of the products showed significant peaks at 192, 175 and 163 ppm. FIG. 4 shows the resulting $^{13}C$ NMR spectra. The peak at 192 ppm could represent an aldehyde group attached to an aromatic ring, which could correspond to the diphenylaldehyde indicated by the results shown in FIG. 2 and FIG. 3. The peak at 163 ppm could be from carboxylic acids while the peak at 175 ppm may be a carboxylic group attached to the aromatic ring. Additionally, the $^{13}C$ NMR spectra did not indicate the presence of any undesirable energetic intermediates.

Examples for Selection of Molar Ratio of $O_3$ to PAH

Two examples are provided below to demonstrate the ability to perform ozonolysis at different initial $O_3$:substrate molar ratios (1:1 and 8:1 respectively) at 8° C. by controlling the total pressure of $O_2/O_3$ and/or the $O_3$ content in $O_2$.

As an example of achieving an initial $O_3$ to substrate molar ratio of 1:1, the following experimental conditions could be used: $O_3$ concentration in $O_2$ is 2 mol %, total reactor pressure (made up of $O_2/O_3$ and $CO_2$ mixtures in the gas phase) is 975 psi (67.2 bar or 6.72 Mpa).

Since the saturation pressure of liquid $CO_2$ at 8° C. is approximately 621 psi (4.28 Mpa), the partial pressure of $O_3$=(6.72–4.28)×2 mol %=0.0488 MPa. According to Henry's law correlation for this system, the concentration of $O_3$ in the liquid phase=2.33 mol/L/MPa×0.0488 Mpa=0.1137 mol/L. Based on a volume of $CO_2$ liquid of 10 mL or 0.01 L, the molar quantity of $O_3$ in the liquid $CO_2$ phase is 0.0011 mol. Therefore, if a molar quantity of the initial substrate is 0.0011 mol (for example, by using 0.2 g of phenanthrene), a molar ratio for $O_3$:substrate of 1:1 can be achieved.

As an example of achieving an initial $O_3$ to substrate molar ratio of 8:1, the following experimental conditions could be used: concentration of $O_3$ in $O_2$ is 6.9 mol % and the total pressure of $O_2/O_3$ and $CO_2$ mixture in the reactor is 1400 psi (96.5 bar or 9.65 MPa).

Since the saturation pressure of liquid $CO_2$ at 8° C. is about 4.28 MPa. The partial pressure of $O_3$=(9.65-4.28)×6.9 mol %=0.3705 MPa By Henry's Law: Concentration of $O_3$ in the liquid phase=2.33 mol/L/MPa×0.3705 Mpa=0.8633 mol/L. Based on a volume of $CO_2$ liquid of 10 mL or 0.01 L, the molar quantity of $O_3$ in the liquid $CO_2$ phase is 0.0086 mol. Therefore, if a molar quantity of the initial substrate is 0.0011 mol (for example, by using 0.2 g of phenanthrene), a molar ratio for $O_3$:substrate of 8:1 can be achieved.

Additional Embodiments

Embodiment 1. A method for conversion of polycyclic aromatic hydrocarbons, comprising: exposing a feedstock comprising one or more polycyclic aromatic hydrocarbons to ozonolysis conditions in a reactor volume comprising liquid $CO_2$ to convert at least a portion of the one or more polycyclic aromatic hydrocarbons into oxygenated conversion products, the ozonolysis conditions comprising a temperature of –25° C. to 50° C. and a pressure of 1.0 MPa-a to 15 MPa-a, a molar ratio of $O_3$ to the one or more polycyclic aromatic hydrocarbons in the reaction medium being 0.1 or more.

Embodiment 2. The method of Embodiment 1, wherein the ozonolysis conditions comprise a pressure of greater than 7.4 MPa-a and a temperature of 31° C. or less; or wherein the ozonolysis conditions comprise a temperature of 0° C. to 31° C.; or a combination thereof.

Embodiment 3. The method of any of the above embodiments, wherein the oxygenated conversion products comprise 1.0 wt % or less of water.

Embodiment 4. The method of any of the above embodiments, wherein $O_3$ is introduced into the reactor volume as a mixture of $O_3$ and $O_2$ comprising 1.0 vol % to 20 vol % $O_3$ relative to a volume of the mixture.

Embodiment 5. The method of any of the above embodiments, wherein the ozonolysis conditions comprise a molar ratio of $O_3$ to the one or more polycyclic aromatic hydrocarbons of 1.0 to 50.

Embodiment 6. The method of any of the above embodiments, wherein the feedstock comprises at least one polycyclic aromatic hydrocarbon comprising one or more non-aromatic rings; or wherein the feedstock comprises at least one polycyclic aromatic hydrocarbon comprising three or more aromatic rings; or a combination thereof.

Embodiment 7. The method of any of the above embodiments, wherein the feedstock further comprises one or more hydrocarbons different from the one or more polycyclic aromatic hydrocarbons, the ozonolysis conditions comprising a molar ratio of $O_3$ to total hydrocarbons in the feedstock of 0.1 to 50.

Embodiment 8. The method of any of the above embodiments, wherein the feedstock comprises at least a portion of a deasphalter rock, at least a portion of an aromatic extract fraction, or a combination thereof.

Embodiment 9. The method of any of the above embodiments, wherein the ozonolysis conditions comprise a concentration in the reaction medium of 1.0 moles or less of the one or more polycyclic aromatic hydrocarbons per liter of $CO_2$.

Embodiment 10. The method of any of the above embodiments, wherein the exposing comprises exposing the one or more polycyclic aromatic hydrocarbons to ozonolysis conditions in a continuous process in a reactor to form a conversion effluent, the method further comprising recycling a portion of the conversion effluent back to the reactor.

Embodiment 11. The method of any of the above embodiments, wherein the feedstock comprises 5.0 wt % to 25 wt % of the one or more polycyclic aromatic hydrocarbon, or wherein the feedstock comprises 60 wt % or more of the one or more polycyclic aromatic hydrocarbons.

Embodiment 12. The method of any of the above embodiments, wherein the reactor volume comprises 90 wt % or more $CO_2$.

Embodiment 13. The method of any of the above embodiments, wherein the reactor volume further comprises a co-solvent, a molar ratio of co-solvent to $CO_2$ in the reactor volume being 0.1 to 0.15, the co-solvent optionally comprising acetic acid.

Embodiment 14. The method of any of the above embodiments, wherein the ozonolysis conditions comprise a single pass conversion of the one or more polycyclic aromatic hydrocarbons of 10 wt % or more relative to a weight of the one or more polycyclic aromatic hydrocarbons.

Embodiment 15. An ozonolysis product comprising oxygenated conversion products formed according to the method of any of Embodiments 1 to 14.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A method for conversion of polycyclic aromatic hydrocarbons, comprising:

exposing a feedstock comprising one or more polycyclic aromatic hydrocarbons to ozonolysis conditions in a reactor volume comprising liquid $CO_2$ to convert at least a portion of the one or more polycyclic aromatic hydrocarbons into oxygenated conversion products, the ozonolysis conditions comprising a temperature of −25° C. to 50° C. and a pressure of 1.0 MPa-a to 15 MPa-a, a molar ratio of $O_3$ to the one or more polycyclic aromatic hydrocarbons in the reaction medium being 0.1 or more.

2. The method of claim 1, wherein the ozonolysis conditions comprise a pressure of greater than 7.4 MPa-a and a temperature of 31° C. or less.

3. The method of claim 1, wherein the oxygenated conversion products comprise 1.0 wt % or less of water.

4. The method of claim 1, wherein $O_3$ is introduced into the reactor volume as a mixture of $O_3$ and $O_2$ comprising 1.0 vol % to 20 vol % $O_3$ relative to a volume of the mixture.

5. The method of claim 1, wherein the ozonolysis conditions comprise a molar ratio of $O_3$ to the one or more polycyclic aromatic hydrocarbons of 1.0 to 50.

6. The method of claim 1, wherein the feedstock comprises at least one polycyclic aromatic hydrocarbon comprising one or more non-aromatic rings.

7. The method of claim 1, wherein the feedstock comprises at least one polycyclic aromatic hydrocarbon comprising three or more aromatic rings.

8. The method of claim 1, wherein the feedstock further comprises one or more hydrocarbons different from the one or more polycyclic aromatic hydrocarbons.

9. The method of claim 8, wherein the ozonolysis conditions comprise a molar ratio of $O_3$ to total hydrocarbons in the feedstock of 0.1 to 50.

10. The method of claim 1, wherein the feedstock comprises at least a portion of a deasphalter rock, at least a portion of an aromatic extract fraction, or a combination thereof.

11. The method of claim 1, wherein the ozonolysis conditions comprise a concentration in the reaction medium of 1.0 moles or less of the one or more polycyclic aromatic hydrocarbons per liter of $CO_2$.

12. The method of claim 1, wherein the exposing comprises exposing the one or more polycyclic aromatic hydrocarbons to ozonolysis conditions in a continuous process in a reactor to form a conversion effluent, the method further comprising recycling a portion of the conversion effluent back to the reactor.

13. The method of claim 1, wherein the feedstock comprises 5.0 wt % to 25 wt % of the one or more polycyclic aromatic hydrocarbons.

14. The method of claim 1, wherein the feedstock comprises 60 wt % or more of the one or more polycyclic aromatic hydrocarbons.

15. The method of claim 1, wherein the reactor volume comprises 90 wt % or more $CO_2$.

16. The method of claim 1, wherein the reactor volume further comprises a co-solvent.

17. The method of claim 16, wherein the co-solvent comprises acetic acid.

18. The method of claim 16, wherein a molar ratio of co-solvent to $CO_2$ in the reactor volume is 0.01 to 0.15.

19. The method of claim 1, wherein the ozonolysis conditions comprise a single pass conversion of the one or more polycyclic aromatic hydrocarbons of 10 wt % or more relative to a weight of the one or more polycyclic aromatic hydrocarbons.

20. The method of claim 1, wherein the ozonolysis conditions comprise a temperature of 0° C. to 31° C.

* * * * *